United States Patent [19]

Fuchs et al.

[11] 4,248,782
[45] Feb. 3, 1981

[54] PREPARATION OF ε-CAPROLACTAM BY CATALYTIC REARRANGEMENT OF CYCLOHEXANONE-OXIME

[75] Inventors: Hugo Fuchs, Ludwigshafen; Uwe Brand, Rosengarten; Peter Horn, Hirschberg, all of Fed. Rep. of Germany

[73] Assignee: BASF Aktiengesellschaft, Fed. Rep. of Germany

[21] Appl. No.: 78,031

[22] Filed: Sep. 24, 1979

[30] Foreign Application Priority Data

Oct. 14, 1978 [DE] Fed. Rep. of Germany ....... 2844880

[51] Int. Cl.³ .......................................... C07D 201/04
[52] U.S. Cl. ............................................. 260/239.3 A
[58] Field of Search ................................. 260/239.3 A

[56] References Cited

U.S. PATENT DOCUMENTS

| 3,210,338 | 10/1965 | Huber et al. | 260/239.3 A |
|---|---|---|---|
| 3,350,393 | 10/1967 | Petri et al. | 260/239.3 A |
| 3,623,575 | 1/1972 | Mannsmann et al. | 260/239.3 A |
| 3,833,560 | 9/1974 | Immel et al. | 260/239.3 A |
| 3,849,335 | 11/1974 | Immel et al. | 260/239.3 A |

FOREIGN PATENT DOCUMENTS 1670902  3/1971  Fed. Rep. of Germany ... 260/239.3 A

Primary Examiner—Henry R. Jiles
Assistant Examiner—Robert T. Bond
Attorney, Agent, or Firm—Keil & Witherspoon

[57] ABSTRACT

In a process for the preparation of ε-caprolactam by catalytic rearrangement of cyclohexanone-oxime in the gas phase at from 230° to 450° C. over a supported catalyst, containing boron trioxide, in a fluidized bed, wherein the catalyst is removed from the fluidized bed at the rate at which it becomes spent and is treated, in a fluidized state, with gases containing molecular oxygen at from 600° to 900° C., after which boron trioxide or boric acid is added to the fluidized catalyst, at from 300° to 900° C., before the catalyst is returned to the fluidized bed, the improvement that boron trioxide or boric acid of particle size from 0.05 to 1.5 mm is fed to the fluidized catalyst at one or more points.

7 Claims, No Drawings

PREPARATION OF ε-CAPROLACTAM BY CATALYTIC REARRANGEMENT OF CYCLOHEXANONE-OXIME

The present invention relates to a process for the preparation of ε-caprolactam by catalytic rearrangement of cyclohexanone-oxime in the gas phase at from 230° to 450° C. over a supported catalyst, containing boron trioxide, in a fluidized bed.

In the catalytic rearrangement of cyclohexanone-oxime, carbon-containing decomposition products deposit on the catalyst, thereby limiting its useful life. German Laid-Open Application DOS No. 1,670,902 discloses that catalysts which have become inactive may be regenerated by burning off these deposits by heating at 500°–900° C. in the presence of air. As stated in the said DOS, it is however necessary to make up any loss of boron trioxide before re-using the catalyst. For this reason, a boric acid ester is fed to the fluidized catalyst at from 300° to 600° C., whereupon the ester decomposes and deposits boron trioxide on the catalyst. However, this requires precise control of the decomposition process in order to decompose the volatile boric acid esters to the desired degree. On the other hand, German Laid-Open Application DOS No. 1,670,902 states that instead of the boric acid ester, boric acid or boron trioxide itself can be passed into the fluidized catalyst bed, but points out that this easily leads to caking of the catalyst.

It is an object of the present invention to provide a method of regenerating the catalyst for the rearrangement of cyclohexanone-oxime to ε-caprolactam whereby caking of the catalyst is avoided and at the same time uniform dosing of the catalytic compound is achieved, so that the activity of the catalyst remains the same.

We have found that this object is achieved, in a process for the preparation of ε-caprolactam by catalytic rearrangement of cyclohexanone-oxime in the gas phase at from 230° to 450° C. over a supported catalyst, containing boron trioxide, in a fluidized bed, wherein the catalyst is removed from the fluidized bed at the rate at which it becomes spent and is treated, in a fluidized state, with gases containing molecular oxygen at from 600° to 900° C., after which boron trioxide or boric acid is added to the fluidized catalyst, at from 300° to 900° C., before the catalyst is returned to the fluidized bed, if boron trioxide or boric acid of particle size from 0.05 to 1.5 mm is fed to the fluidized catalyst at one or more points.

The novel process has the advantage that caking of the catalyst bed is avoided and that a uniform catalyst quality is achieved. The process according to the invention allows trouble-free operation for long periods. Furthermore, the novel process is inexpensive and permits reliable dosing of the catalytic compound.

The conditions for the rearrangement of cyclohexanone-oxime to ε-caprolactam are known. Cyclohexanone-oxime vapor or liquid or solid is passed into the fluidized bed containing the catalyst at the reaction temperature. Advantageously, the cyclohexanone-oxime contains from 1 to 10, especially from 3 to 7, % by weight of water. The rearrangement is carried out at from 230° to 450° C., preferably from 270° to 370° C., under atmospheric pressure, reduced pressure or slightly superatmospheric pressure. If reduced pressure is used, the range from 20 to 200 mm Hg is preferred, whilst if superatmospheric pressure is used, the pressure in general does not exceed 2 bar. The catalyst is kept fluidized by means of an inert gas, such as carbon dioxide, argon or nitrogen, the latter being preferred. In general, the inert gas is used in an amount of from 5 to 70 percent by volume, based on the gaseous mixture comprising cyclohexanone-oxime vapor, caprolactam and inert gas, the percentage depending on whether the process is carried out under atmospheric pressure, superatmospheric pressure or reduced pressure; at superatmospheric pressure, more inert gas is used.

It is also advantageous to introduce the inert gas at 80°–300° C. into the fluidized bed, and thus to remove the heat of rearrangement by means of the inert gas which undergoes heating in the fluidized bed.

The catalyst used is a conventional catalyst comprising boron trioxide or boric acid (which is converted to boron trioxide under the reaction conditions) on a carrier. Suitable carriers are, in particular, aluminum oxide in its various modifications, eg. alumina, γ-alumina and boehmite, as well as silica and titanium dioxide, and mixtures of such oxides or of compounds of the oxides with one another, for example aluminum silicates. The weight ratio of boron trioxide to carrier is in general from 1:9 to 1:1. In the preferentially used catalysts, the proportion of boron trioxide is from 25 to 50% by weight. The catalysts may be modified by additives, eg. manganese, cobalt or nickel, in amounts of up to 10% by weight, based on $B_2O_3$ and calculated as metal. They are added during the process of preparation of the catalyst in the form of salts, eg. nitrates or fatty acid salts, which on heating form the corresponding oxides. Accordingly, the finished catalyst contains the metals as oxides or as their compounds with boron trioxide. The catalysts are prepared in the conventional manner. For example, the carriers are impregnated with boric acid or ammonium borate solution, dried at 50°–500° C. and then heated at 600°–1200° C. to convert the applied compounds to the corresponding mixed phases with boron trioxide. The catalysts are molded in the conventional manner, for example by pasting the boron trioxide and carrier with a small amount of water, mixing the paste in a kneader, extruding it to give pills or extrudates, and drying and heating these at the stated temperatures. The particle sizes are advantageously from 0.05 to 1.5 mm, especially from 0.2 to 1.0 mm. The height of the catalyst bed is advantageously selected so that the residence time of the cyclohexanone-oxime therein is from 0.01 to 30 seconds, especially from 0.1 to 5 seconds.

Caprolactam is separated out from the resulting gas, containing ε-caprolactam, by chilling with previously produced caprolactam or stepwise, by first chilling with ε-caprolactam and then with water, in a column. After removing the water, the inert gas is recycled to the fluidized bed.

Catalyst is periodically or, advantageously, continuously taken off the fluidized bed and treated at 600°–900° C. with a gas containing molecular oxygen, especially with air. For this treatment, the catalyst is in a fluidized form. Advantageously, from 0.5 to 10 kg of gas containing molecular oxygen are used per kg of catalyst in the regenerator. As a rule, the treatment time is from 10 minutes to 10 hours, and the amount of catalyst removed per hour from the fluidized bed is from 0.1 to 10 times the amount contained therein, depending on the amount of cyclohexanone-oxime fed in.

The catalyst treated as described is dosed with boron trioxide or broic acid, before being returned to the fluidized bed, in order to compensate for losses of boron trioxide and to restore the original catalytic activity. For this purpose, boron trioxide or boric acid, of particle size from 0.05 to 1.5 mm, is fed into the catalyst, which is at 300°–900° C. and is fluidized, at one point or at several points simultaneously. Advantageously, boron trioxide or boric acid is introduced at not less than 2, preferably at from 2 to 5, points.

It has proved particularly advantageous if boron trioxide or broic acid is fed in as a mixture with caprolactam or urea. Such mixtures preferably contain from 10 to 99% by weight of boron trioxide or boric acid, the latter also calculated as boron trioxide. The particle size of the mixture fed in is advantageously from 0.1 to 2 mm.

When dosing the catalyst with the active compounds, the catalyst is kept fluidized by means of air; advantageously, the catalytic compounds are introduced by means of a stream of air into the fluidized catalyst material. The amount of catalytic compounds added depends on the loss of boron trioxide and is in general from 0.1 to 20% by weight, based on the regenerated catalyst.

The catalyst treated in this way is then—preferably after cooling to 400°–300° C.—returned to the fluidized bed for the rearrangement of cyclohexanone-oxime.

Caprolactam prepared by the process of the invention is suitable for the manufacture of polycaprolactam.

The Examples which follow illustrate the process according to the invention.

EXAMPLE 1

About 500 kg of a catalyst consisting of 55% of alumina and 45% of boron trioxide, and having a particle size of from 0.3 to 1.0 mm, are introduced into a reactor having a length of 5,000 mm and a diameter of 1,200 mm. Per hour, 650 kg of nitrogen, which has been heated electrically to 360° C., are blown through a perforated bottom plate into the reactor and the catalyst is thereby fluidized. 400 kg of cyclohexanone-oxime, containing 4% by weight of water, are now introduced per hour, through 2 nozzles, into the fluidized bed. The temperature at which the nitrogen required for fluidizing is introduced is lowered as the temperature in the reactor rises, so as to maintain a reaction temperature of 360° C. The reaction gases are separated and the caprolactam formed is worked up.

Per hour, 200 kg of catalyst are taken from the reactor and passed to a regenerator. There, the catalyst is kept fluidized by blowing-in air, preheated to 700° C., through a perforated bottom plate. The internal temperature is about 800° C. The amount of air required is about 700 kg/hour. The impurities present on the catalyst burn away. In a further fluidized bed, the regenerated catalyst is cooled to about 400° C. by blowing colder air into it. This cooling reactor has a length of 3,500 mm and a diameter of 1,400 mm. About 4 kg per hour of boric acid of particle size 0.3–1 mm are introduced into the fluidized bed through 2 nozzles located 180 mm above the bottom plate, by first feeding the boric acid, by means of a metering screw, to a gas jet conveyor for solids, and conveying it into the fluidized bed with about 500 kg of air/hour.

The boron trioxide content of the catalyst is in this way maintained at 42–44%. Without constant replenishment of boric acid, the catalyst loses about 1% of boron trioxide per day.

Over a period of 4 weeks, no caking of the catalyst is found.

EXAMPLE 2

The procedure described in Example 1 is followed but instead of boric acid, a mixture of boric acid and urea in the weight ratio of 80:20 is injected into the fluidized bed cooler. The particle size of the mixture is from 0.8 to 1.5 mm, and the mixture is introduced through 4 nozzles arranged at equal intervals around the fluidized bed cooler. The mixture of urea and boric acid has a melting range of from 145° to 176° C. The amount of mixture introduced per hour is 5 kg. In this way, the boron trioxide content of the catalyst is kept at 43–45% over 3 weeks.

EXAMPLE 3

The procedure described in Example 1 is followed, but instead of boric acid a mixture of boron trioxide and caprolactam in the weight ratio of 80:20 is fed to the catalyst through 2 nozzles. The amount fed in per hour at both points together is about 3 kg. The boron trioxide content of the catalyst remains at about 41–42%.

We claim:

1. In a process for the preparation of ε-caprolactam by catalytic rearrangement of cyclohexanone-oxime in the gas phase at from 230° to 450° C. over a supported catalyst, containing boron trioxide, in a fluidized bed, wherein the catalyst is removed from the fluidized bed at the rate at which it becomes spent and is treated, in a fluidized state, with gases containing molecular oxygen at from 600° to 900° C., after which boron trioxide or boric acid is added to the fluidized catalyst, at from 300° to 900° C., before the catalyst is returned to the fluidized bed, the improvement wherein particles consisting of boron trioxide or boric acid of particle size from 0.05 to 1.5 mm are fed to the fluidized catalyst at one or more points.

2. A process as claimed in claim 1, wherein said particles of boron trioxide or boric acid mixed with caprolactam and/or urea are fed to the catalyst.

3. A process as claimed in claim 2, wherein a mixture of from 10 to 99% by weight of boric acid (calculated as boron trioxide) or boron trioxide with caprolactam and/or urea is used.

4. A process as claimed in claim 1 wherein said particles consist of particles of boric acid.

5. A process as claimed in claim 1 wherein said particles consist of particles of boron trioxide.

6. A process as claimed in claim 5 wherein the amount of boron trioxide fed is in the range of 0.1 to 20% by weight, based on the regenerated, supported catalyst.

7. A process as claimed in claim 4 wherein the amount of boric acid fed is in the range of 0.1 to 20% by weight, based on the regenerated, supported catalyst.

* * * * *